US00PP27663P3

(12) United States Plant Patent
Wood

(10) Patent No.: US PP27,663 P3
(45) Date of Patent: Feb. 14, 2017

(54) ***PHYSOCARPUS* 'POIPD2'**

(50) Latin Name: *Physocarpus opulifolius*
Varietal Denomination: POIPD2

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/756,873

(22) Filed: Oct. 21, 2015

(65) Prior Publication Data

US 2016/0128258 P1 May 5, 2016

Related U.S. Application Data

(60) Provisional application No. 62/122,540, filed on Oct. 22, 2014.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Cassandra Bright

(57) ABSTRACT

A new and distinct *Physocarpus* cultivar named 'POIPD2' is disclosed, characterized by a smaller plant size, with a round, compact habit. Foliage is small and distinctively burgundy. Plants exhibit good mildew resistance. The new variety is a *Physocarpus*, normally produced as an outdoor garden or container plant.

2 Drawing Sheets

Latin name of the genus and species:
*Physocarpus opulifolius*
Variety denomination: 'POIPD2'.

BACKGROUND OF THE INVENTION

The new *Physocarpus* cultivar is a product of a planned breeding program conducted by the inventor, Timothy D. Wood, in Grand Haven, Minn. The objective of the breeding program was to produce new *Physocarpus* varieties with unique foliage. The cross resulting in this new variety was made during June of 2005.

The seed parent is the unpatented, unnamed *Physocarpus opulifolius* subsp. *intermedius f. parvifolius*. The pollen parent is the unpatented, *Physocarpus opulifolius* 'D#2'. The new variety was identified as a potentially interesting selection in May of 2008, at a nursery in Spring Lake, Minn.

Asexual reproduction of the new cultivar 'POIPD2' by softwood cuttings was first performed during Summer of 2008, at commercial greenhouse in Grand Haven, Minn. Subsequent propagation has shown that the unique features of this cultivar are stable and reproduced true to type in 5 successive generations.

SUMMARY OF THE INVENTION

The cultivar 'POIPD2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'POIPD2' These characteristics in combination distinguish 'POIPD2' as a new and distinct *Physocarpus* cultivar:

1. Smaller plant size.
2. Small, dark burgundy leaves.

3. Attractive, rounded compact habit.
4. Good mildew resistance.

PARENT COMPARISON

Plants of the new cultivar 'POIPD2' are similar to plants of the seed parent, *Physocarpus opulifolius* subsp. *intermedius f. parvifolius* in most horticultural characteristics, however, plants of the new cultivar 'POIPD2' differs in the following:

1. Burgundy leaves, the parent has green leaves.
2. Larger plant size, parent is more dwarf in nature.
3. Larger leaves.
4. Rounded plant habit, the parent is low, mounded and arching in form.

Plants of the new cultivar 'POIPD2' are similar to plants of the pollen parent, *Physocarpus opulifolius* 'D#2' in most horticultural characteristics, however, plants of the new cultivar 'POIPD2' differs in the following:

1 Darker leaf color.

COMMERCIAL COMPARISON

Plants of the new cultivar 'POIPD2' can also be compared to the commercial variety *Physocarpus* 'Seward', U.S. Plant Pat. No. 14,821. These varieties are similar in most horticultural characteristics; however 'POIPD2' differs in the following:

1. Lighter leave color.
2. Less compact.

BRIEF DESCRIPTION OF THE PHOTOGRAPHS

Figure 1:
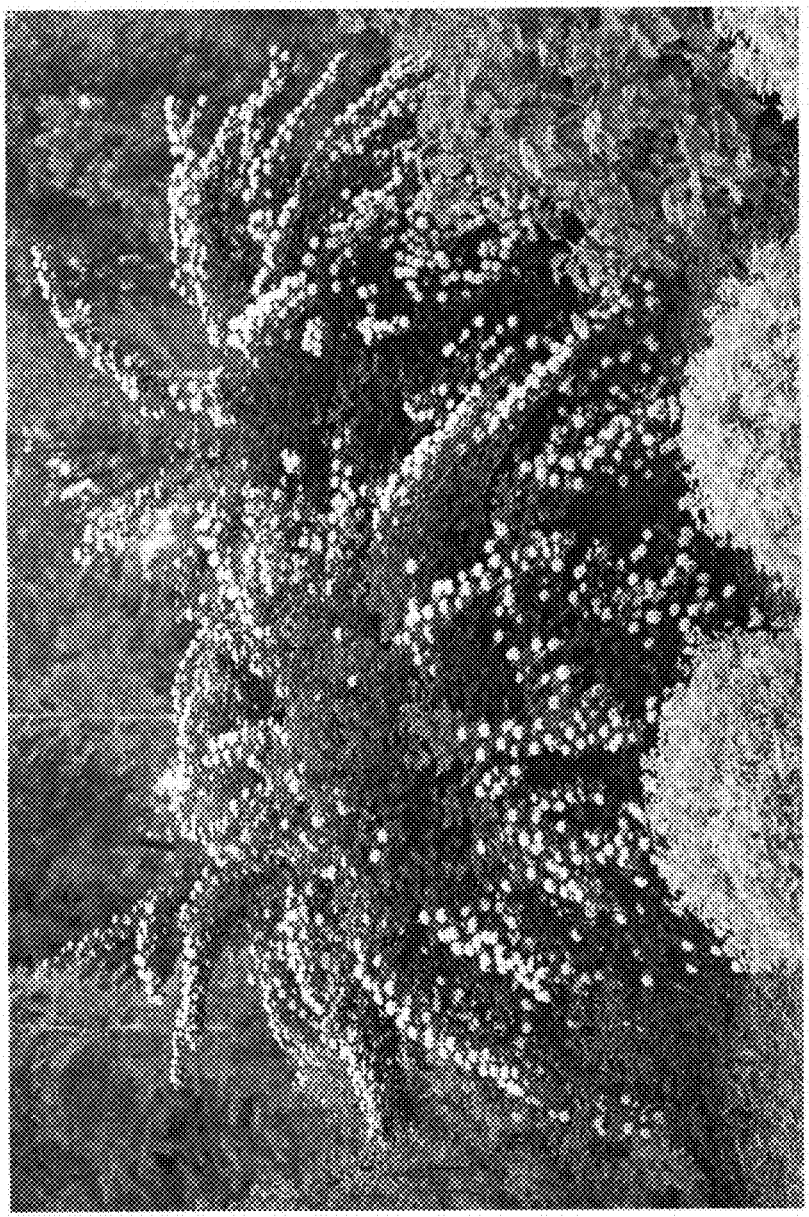

The accompanying photograph in FIG. 1 illustrates in full color a typical mature plant of 'POIPD2'.

Figure 2:
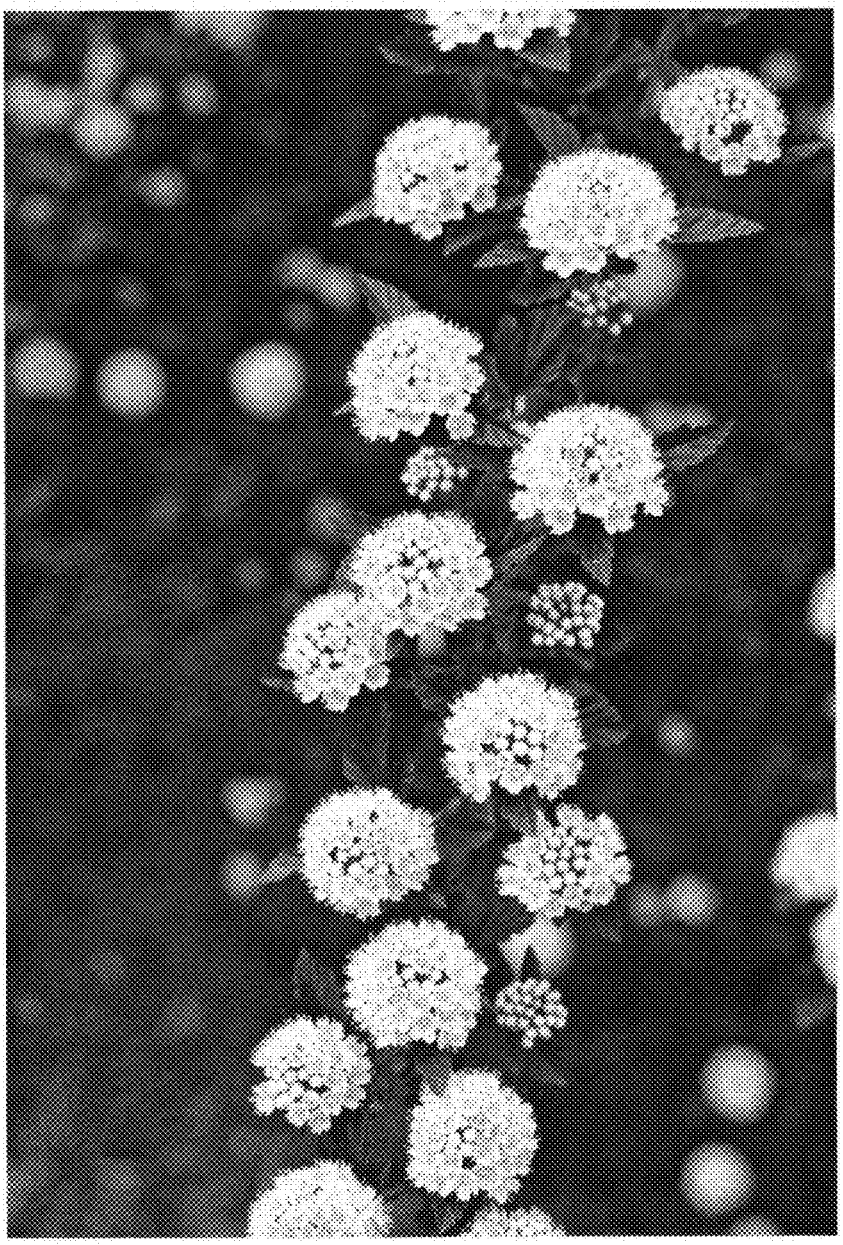

FIG. 2 illustrates in full color a typical inflorescence of 'POIPD2' grown outdoors in Grand Haven, Minn., in a garden setting. Age of the plant photographed is approximately 4 years from a young plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'POIPD2' plants grown outdoors in Grand Haven, Minn. This occurred during June of 2014. The plants were between 1 to 2 years old grown in 1 gallon containers. The growing temperature ranged from −30° C. to 37° C. The garden is un-shaded, giving bright, normal sunlight conditions. Measurements and numerical values represent averages of typical plant types.

Botanical classification: *Physocarpus opulifolius* 'POIPD2'.

PROPAGATION

Time to initiate roots: About 15 days at approximately 25° C.

Root description: Fine, and freely branching.

Time to produce a liner: About 65 days at 25° C.

PLANT

Plant type: Shrub perennial.

Age of plant described: Approximately 1 to 2 years old.

Growth habit: Upright and outward.

Pot size of plant described: 1 gallon pot.

Height: Approximately 25 cm to top of foliage.

Plant spread: Approximately 20 cm.

Growth rate: Rapid.

Plant vigor: Strong.

Branching characteristics: When pinched branches form at every internode.

Length of primary lateral branches: Approximately 25 cm.

Diameter of lateral branches: Approximately 3 cm.

Quantity of lateral branches: Average 10.

Stem:

*Stem color*.—Near RHS Greyed-purple 183A.

*Bark color*.—Near RHS Brown 200C.

Internode length: Average 3.6 cm.

FOLIAGE

Leaf:

*Arrangement*.—Alternate, single.

*Average length*.—Approximately 5.5 cm.

*Average width*.—Approximately 5.3 cm.

*Shape of blade*.—Ovate, deeply lobed with three lobes per leaf.

*Apex*.—Acute.

*Base*.—Cordate-Obtuse.

*Attachment*.—Stalked.

*Margin*.—Serrate-dentate.

*Texture of top surface*.—Smooth, glabrous.

*Texture of bottom surface*.—Veins protrude, smooth between veins.

*Color*.—Young foliage upper side: Near RHS Greyed-purple 187B. Young foliage under side: Combination of Near RHS Yellow-green 148A and Greyed-purple 187B. Mature foliage upper side: Near RHS Greyed-purple 187B overlaying Yellow-green 147A. Mature foliage under side: Near RHS Greyed-purple 187B overlaying Yellow-green 147A.

*Venation*.—Type: Pinnate. Venation color upper side: Near RHS Green 131A. Venation color under side: Near RHS Yellow-green 147C.

*Petiole*.—Average Length: Approximately 3.1 cm. Diameter: Approximately 1-1.5 mm. Petiole color upper side: Ridges near RHS Brown 200B; Center near RHS Yellow-green 147C. Petiole color lower side: Near RHS Yellow-green 147C. Petiole Texture upper side; Two ridges run on the edges of the petiole, otherwise smooth. Petiole Texture lower side; Glabrous.

FLOWER

Natural flowering season: Spring.

Inflorescence type and habit: Corymb.

Flower longevity on plant: Individual flowers last approximately 2 to 3 days on the plant. Each corymb lasts approximately 4 weeks with flowers.

Quantity of flowers per inflorescence: About 28.

Inflorescence size:

*Width*.—Approximately 4 cm.

*Height*.—Approximately 2.5 cm.

Quantity of flowers per lateral stem: Hundreds.

Quantity of flowers per plant: Thousands.

Individual flowers:

*Flower form*.—Cupped.

*Flower aspect*.—Upright.

*Size*.—Diameter: Approximately 4-5 mm. Length: Approximately 4 mm. Depth: 4 mm. Persistence: Self cleaning.

Petal:

*Petal arrangement*.—Whorl.

*Number of petals per flower*.—5.

*Petal appearance*.—Smooth, opaque.

*Petal shape*.—Rounded and obovate.

*Margin*.—Entire.

*Tip shape*.—Obovate.

*Length*.—2 mm.

*Width*.—2 mm.

*Texture*.—Upper: Smooth. Lower: Smooth.

Petal color:

*When opening*.—Upper surface: Near RHS Red 49C. Lower surface: Near RHS Red 49C.

*Fully opened*.—Upper surface: Near RHS White 155D. Lower surface: Near RHS White 155D.

*Fading*.—Upper surface: Near RHS White 155D. Lower surface: Near RHS White 155D.

Bud:

*Shape*.—Obovate.

*Length*.—Approximately 2 mm.

*Diameter*.—Approximately 1.5 mm.

*Color*.—Near RHS Red 49D.

Sepals:

*Shape*.—Lanceolate.

*Arrangement*.—Whorl.

*Length*.—Approximately 2 mm.

*Width*.—Approximately 1 mm.

*Margin*.—Entire.
*Base*.—Fused.
*Tip*.—Acuminate.
*Texture*.—Smooth.
*Color*.—Immature: Near RHS Green 138A, heavily flushed Purple N79A. Mature: Near RHS Yellow-green 146C at base and Near RHS Red 51A at tip.

Peduncle:
*Length*.—Average 1.5 cm.
*Diameter*.—1 mm.
*Color*.—Near RHS Yellow-green 146C.
*Orientation*.—Upright, straight.
*Strength*.—Good.
*Texture*.—Smooth.

REPRODUCTIVE ORGANS

Stamens:
*Number*.—25-28.
*Filament length*.—Approximately 1 mm.
*Filament color*.—Near RHS White 155D.

Anthers:
*Shape*.—Elliptic to round.
*Length*.—Approximately 0.5 mm.
*Color*.—Near RHS Red 50C and Yellow-orange 18A.
*Pollen*.—Some.

Pistil:
*Number*.—Average of 4.
*Length*.—Approximately 0.25 mm.
*Style*.—Length: Approximately 0.5 cm. Color: Near RHS Red-Purple 73D.
*Stigma*.—Shape: Globular. Color: Near RHS Yellow-green 146D. Ovary color: Near RHS Green 137B.

OTHER CHARACTERISTICS

Seeds and fruits: Not observed to date.
Garden performance: Very good.
Disease/pest resistance: Neither resistance nor susceptibility to pathogens and pests common to *Physocarpus* have been observed.
Temperature tolerance: The new variety tolerates temperatures between −30 to 37° C.

What is claimed is:

1. A new and distinct cultivar of *Physocarpus* plant named 'POIPD2' as herein illustrated and described.

* * * * *